United States Patent
Goldzak et al.

(10) Patent No.: US 9,301,791 B2
(45) Date of Patent: Apr. 5, 2016

(54) OSTEOSYNTHESIS PIN

(75) Inventors: Mario Goldzak, Balma (FR); Patrick Simon, Lyons (FR); Thomas Mittlmeier, Berlin (DE); Franck Hunt, Quimper (FR)

(73) Assignees: FOURNITURES HOSPITALIERES INDUSTRIE (FR); Mario Goldzak (FR); Patrick Simon (FR); Thomas Mittlmeier (FR)

( * ) Notice: Subject to any disclaimer, the term of this patent is extended or adjusted under 35 U.S.C. 154(b) by 56 days.

(21) Appl. No.: 13/989,132

(22) PCT Filed: Nov. 11, 2011

(86) PCT No.: PCT/FR2011/052618
§ 371 (c)(1),
(2), (4) Date: Aug. 13, 2013

(87) PCT Pub. No.: WO2012/069727
PCT Pub. Date: May 31, 2012

(65) Prior Publication Data
US 2013/0317556 A1 Nov. 28, 2013

(30) Foreign Application Priority Data
Nov. 25, 2010 (FR) ...................... 10 59724

(51) Int. Cl.
| A61B 17/04 | (2006.01) |
| A61B 17/84 | (2006.01) |
| A61F 2/08 | (2006.01) |
| A61B 17/86 | (2006.01) |
| A61B 17/72 | (2006.01) |

(52) U.S. Cl.
CPC ........... *A61B 17/864* (2013.01); *A61B 17/7258* (2013.01); *A61B 17/7291* (2013.01); *A61B 17/7233* (2013.01)

(58) Field of Classification Search
USPC ............................................. 606/96–98, 104
See application file for complete search history.

(56) References Cited

U.S. PATENT DOCUMENTS

| 6,558,388 B1 | 5/2003 | Bartsch et al. |
| 2007/0270845 A1* | 11/2007 | Watanabe et al. ............... 606/62 |
| 2007/0288016 A1 | 12/2007 | Halder |
| 2010/0114315 A1 | 5/2010 | Manderson |

FOREIGN PATENT DOCUMENTS

| EP | 0922437 A1 | 6/1999 |
| WO | 2006091460 A1 | 8/2006 |
| WO | 2007125497 A1 | 11/2007 |

OTHER PUBLICATIONS

International Search Report issued Jan. 23, 2012 re: PCT/FR2011/052618; citing: U.S. Pat. No. 6,558,388 B1, US 2007/288016 A1, US 2010/114315 A1, EP 0 922 437 A1, WO 2006/0091460 A1 and WO 2007/125497 A1.

* cited by examiner

Primary Examiner — Sameh Boles
(74) Attorney, Agent, or Firm — Cantor Colburn LLP

(57) ABSTRACT

The invention relates to an osteosynthesis pin, in particular for a fracture of a calcaneum, made up of a generally cylindrical hollow body comprising an axial bore extending over the entire length thereof, a plurality of through-holes staggered longitudinally relative to one another and intended for attachment screws to pass therethrough, and at least one oblong opening suitable for an ancillary instrument to pass therethrough for repositioning fractured bone fragments.

10 Claims, 2 Drawing Sheets

OSTEOSYNTHESIS PIN

TECHNICAL FIELD

The present invention relates to an osteosynthesis pin or osteosynthesis nail, and more particularly an osteosynthesis pin for a fracture of a calcaneum.

BACKGROUND

Different operating techniques exist to consolidate a bone fracture, and more particularly a fracture of a calcaneum.

A first known technique consists of immobilizing the patient's foot in a cast. Such a technique avoids any risk of infection for the patient, but can only be used for simple fractures, i.e., without moving fractured bone fragments.

Complex fractures, i.e., that require moving fractured bone fragments, must be treated surgically using various osteosynthesis means.

A first surgical technique consists of inserting traditional osteosynthesis screws or so-called "compression" osteosynthesis screws into the fractured bone fragments so as to secure the latter to the main part of the bone in order to allow natural bone consolidation of the fracture site. Such screws may be placed percutaneously, and therefore do not require a large cutaneous incision. However, in order to ensure satisfactory stabilization of the fractured bone fragments, it is often necessary to provide for the placement of several osteosynthesis screws per fractured bone fragment.

A second surgical technique consists of implanting, in the patient's foot, an osteosynthesis plate using the external lateral approach. The implantation of such an osteosynthesis plate makes it possible to ensure satisfactory stabilization of the fractured bone fragments, but often leads to cutaneous complications, or even necroses. Furthermore, the implantation of such an osteosynthesis plate requires a large cutaneous incision, which increases the risks of infection for the patient.

BRIEF SUMMARY

The present invention aims to resolve these drawbacks.

The technical problem at the base of the invention therefore comprises providing an osteosynthesis pin or osteosynthesis nail that has a simple and cost-effective structure, while limiting the risks of infection for the patient and favoring bone consolidation.

In that end, the present invention relates to an osteosynthesis pin, in particular for the fracture of a calcaneum, characterized in that it is made up of a generally cylindrical hollow body comprising an axial bore extending over the entire length thereof, a plurality of through-holes staggered longitudinally relative to one another and intended for attachment screws to pass therethrough, and at least one oblong opening suitable for an ancillary instrument to pass therethrough for repositioning fractured bone fragments.

The structure of the pin according to the invention makes it possible to insert the latter into the patient's bone by making a small cutaneous incision, and thereby limits the risks of infection for the patient.

Furthermore, the presence of the through-holes formed in the body of the pin makes it possible to assemble, stably using osteosynthesis screws, the fractured bone fragments to the main part of the bone in which the pin is implanted.

The presence of the axial bore and the at least one oblong opening formed in the body in particular allow the insertion of a curved ancillary instrument, such as a graft remover, or a curved pin inside the body from the outside of the foot and the passage of the free end thereof through the opening so as to cooperate with the fractured fragments to put them back into place. The presence of the axial bore and the at least one oblong opening also allows the passage of an arthroscopic camera so as to verify that replacement of the fractured fragments.

Further, the fact that the body includes an axial bore extending over the entire length thereof makes it possible to reposition the bone cylinder obtained during the preparation of the bone designed to receive the pin, i.e., during the performance of bone drilling designed to receive the pin, inside the body, which then acts as an arthrodesis cage. These arrangements make it possible to further improve the bone consolidation, and also to decrease the convalescence of the patient.

Preferably, the body includes two diametrically opposite oblong openings.

Advantageously, each opening extends over a length corresponding substantially to at least 40% of the length of the pin.

Advantageously, each opening extends substantially parallel to the axis of the pin.

Preferably, each through-hole has an axis extending substantially perpendicular to the axis of the pin, and the axes of the through-holes are substantially parallel.

Advantageously, each opening is oriented at an angle comprised between 80 and 100° relative to the axes of the through-holes of the pin, and preferably approximately 90°.

Preferably, the distal end of the body comprises at least one tooth arranged to cooperate with the bone during the insertion of the pin therein.

The body advantageously includes angular indexing means for an ancillary instrument designed to place said pin, the indexing means preferably being positioned at the proximal end of the pin. The indexing means for example include an indexing slot emerging in the proximal end of the pin and with an axis substantially parallel to the axis of the through-holes.

According to one embodiment, the body comprises fastening means designed to cooperate with complementary fastening means provided on an ancillary instrument designed to place said pin. The axial bore for example comprises a threaded portion forming the fastening means. The threaded portion is advantageously positioned near the proximal end of the body. Preferably, the inner diameter of the body at the apices of the threads substantially corresponds to the inner diameter of the body outside the threaded portion.

Advantageously, the through-holes are longitudinally staggered equidistantly. The through-holes are for example suitable for the passage of fastening screws with a diameter comprised between 4 and 6 mm. The body advantageously has between two and four through-holes.

The body is preferably made from a biocompatible material, such as stainless steel or titanium alloy. The body has a length for example comprised between 30 and 70 mm, and an outer diameter for example comprised between 8 and 15 mm.

The body advantageously has a substantially constant inner diameter over its entire length.

BRIEF DESCRIPTION OF THE DRAWINGS

In any case, the invention will be well understood using the following description, done in reference to the appended diagrammatic drawing showing, as non-limiting examples, several embodiments of said osteosynthesis pin.

DETAILED DESCRIPTION

Figure 1:
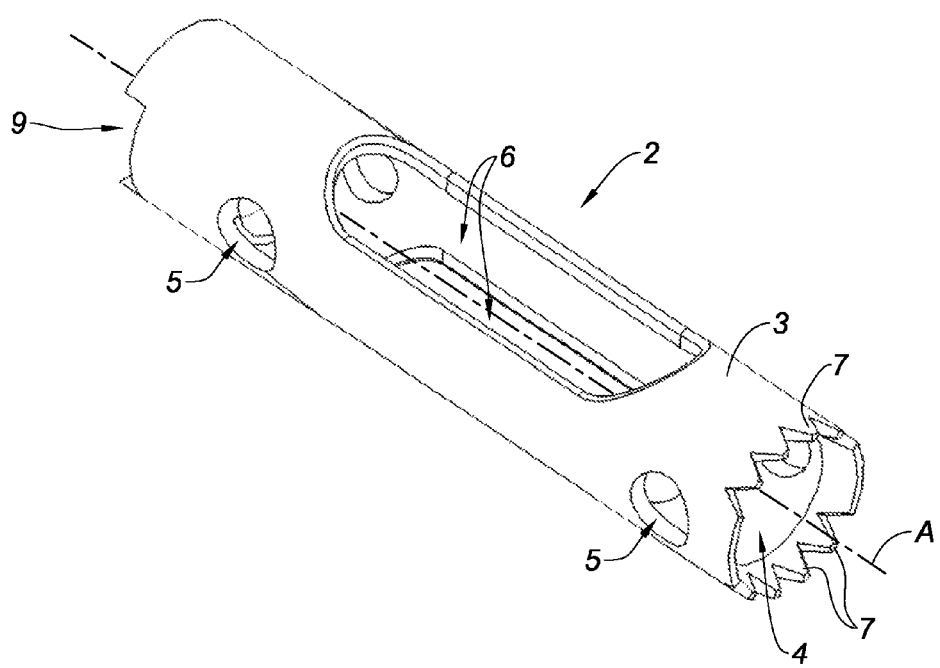
FIG. 1 is a perspective view of an osteosynthesis pin or osteosynthesis nail according to the invention.
Figure 2:
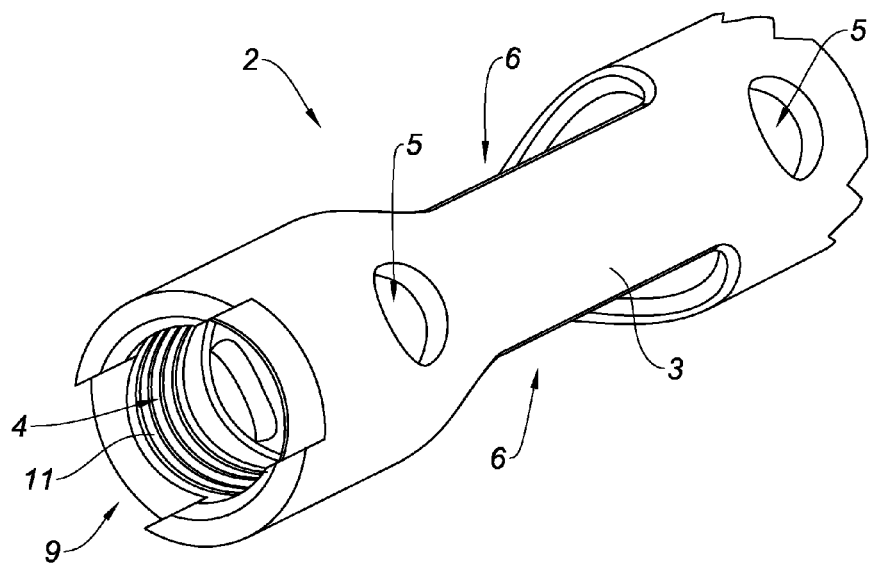
FIG. 2 is a rear perspective view of the pin of FIG. 1.

FIGS. 1 and 2 show an osteosynthesis pin 2 or osteosynthesis nail 2 for a fracture of a calcaneum.

The osteosynthesis pin 2 comprises a generally cylindrical hollow body 3. The body 3 has a length for example comprised between 30 and 70 mm, and is made from a biocompatible material, such as stainless steel or titanium alloy. The body advantageously has an outer diameter comprised between 8 and 15 mm.

The hollow body 3 includes an axial bore 4 extending over the entire length thereof, with a substantially circular cross-section.

The hollow body 3 includes an axial bore 4 extending over the entire length thereof, and with a substantially circular cross-section.

The hollow body 3 also includes a plurality of through-holes 5 longitudinally staggered relative to one another and designed for the passage of fastening screws. The axes of the through-holes 5 are substantially parallel to each other and extend substantially perpendicular to the axis A of the pin.

The body 3 advantageously has between two and four through-holes 5. The through-holes 5 are preferably suitable for the passage fastening screws with a diameter comprised between 4 and 6 mm. Advantageously, when the hollow body 3 has a least three through-holes 5, the latter are longitudinally staggered equidistantly.

The hollow body 3 also includes two diametrically opposite oblong openings 6 each suitable for the passage of an ancillary instrument designed to reposition fractured bone fragments, such as a curved graft remover or a curved pin.

Each oblong opening 6 extends substantially parallel to the axis A of the pin, and has a length substantially corresponding to at least 40% of the length of the pin.

As shown more particularly in FIG. 1, each oblong opening 6 is oriented at an angle comprised between 80 and 100° relative to the axes of the through-holes 5 of the pin, and preferably approximately 90°.

The distal end of the body 3, i.e., the end of the body designed to be introduced into the bone first, comprises a plurality of teeth 7 arranged to cooperate with the bone during the insertion of the pin 2 therein.

The body 3 also includes angular indexing means of an ancillary instrument 8 designed to place said pin. The indexing means advantageously include an indexing slot 9 emerging in the proximal end of the pin and with an axis substantially parallel to the axis of the through-pins 5.

The body 3 also includes fastening means designed to cooperate with complementary fastening means provided on the ancillary instrument designed to place said pin.

As shown in FIG. 2, the axial bore 4 comprises a threaded portion 10 positioned near the proximal end of the body, the threaded portion 10 forming the fastening means. Preferably, the inner diameter of the body 3 at the apices of the threads of the threaded portion 10 corresponds substantially to the inner diameter of the body outside the threaded portion. Thus, the body 3 has a substantially constant inner diameter over the entire length thereof.

According to one alternative embodiment of the invention not shown in the figures, the body 3 may include four through-holes 5 with equidistant axes, and the number and profile of the teeth 7 may be different.

During an osteosynthesis operation aiming to attach a plurality of bone fragments to the body of the corresponding calcaneum, a surgeon proceeds as follows.

First, the surgeon drills in the calcaneum, and more particularly in the large calcaneal tuberosity, using a drill with an inner diameter substantially corresponding to the inner diameter of the body 3. The drilling is preferably done along the axis of the trabeculae.

Next, the surgeon inserts the pin 2 inside the bone borehole using a suitable ancillary instrument. Advantageously, the pin 2 is rotated using that ancillary instrument during insertion into the borehole, such that the teeth 7 of the pin cooperate with the calcaneum so as to slightly enlarge the diameter of the bone borehole. It should be noted that the pin 2 is positioned in the bone borehole such that the axes of the through-holes 5 extend in a plane substantially parallel to the lower surface of the foot.

Figure 3:
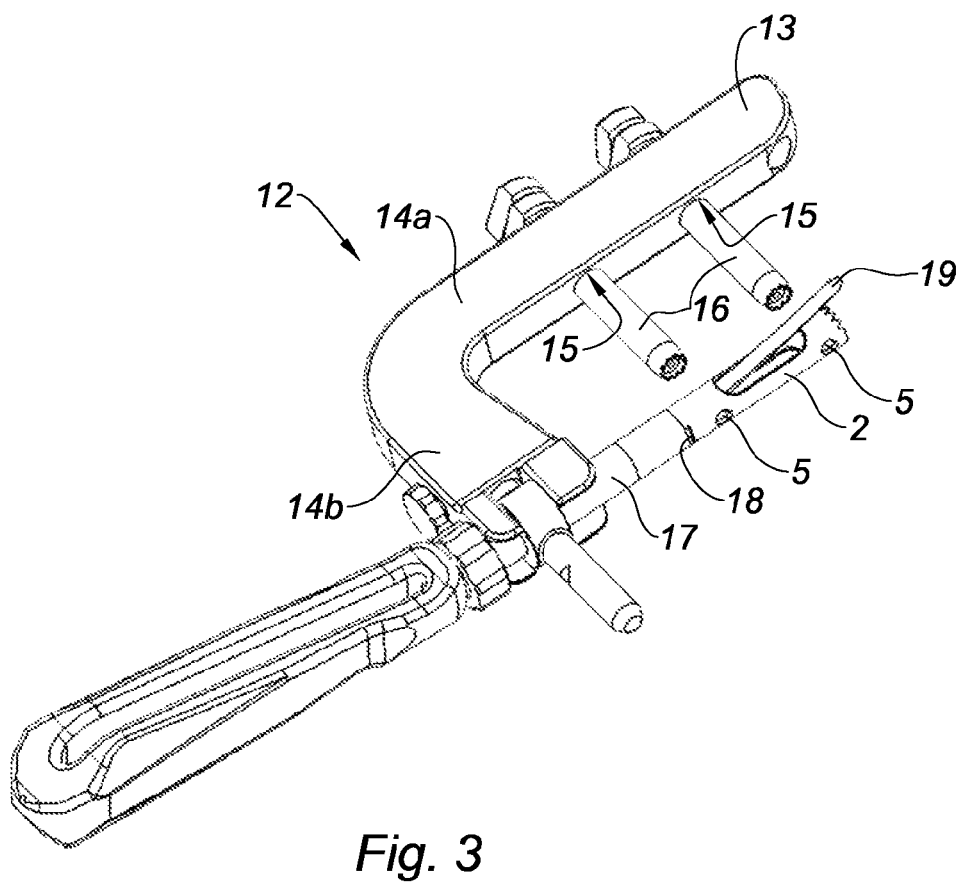
FIGS. 3 and 4 are perspective views of the pin of FIG. 1 mounted on an ancillary instrument suitable for placing said pin.
Figure 4:
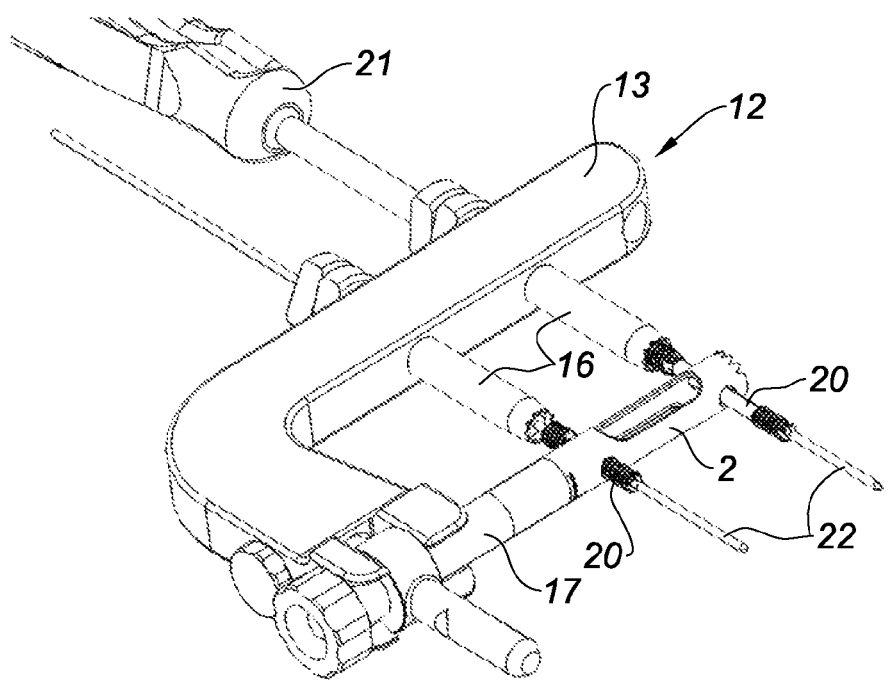

Then, the surgeon fixes an ancillary instrument 12, as shown in FIGS. 3 and 4, on the pin 2 previously implanted in the calcaneum.

The ancillary instrument 12 includes a generally L-shaped guide portion 13 having a first branch 14a including a plurality of through-openings 15 staggered relative to one another and designed for the passage of a drill bushing 16, and a second branch 14b perpendicular to the first branch. The ancillary instrument 12 also comprises a cylindrical portion 17 with an axis parallel to the first branch 14a of the guide portion 13, the cylindrical portion 17 comprising two diametrically opposite angular indexing fingers 18 arranged to cooperate with the indexing slot 9 formed the proximal portion of the pin 2.

The ancillary instrument 12 also comprises immobilizing means designed to make it possible to immobilize the ancillary instrument on the pin 2. The immobilizing means advantageously include a fastening screw (not shown in the figures) extending through the cylindrical portion 17 and arranged to cooperate with the threaded portion 10 formed at the proximal end of the pin.

The surgeon then inserts a curved ancillary instrument 19 into the axial bore 4 of the body 3 from the outside of the foot by passing through the cylindrical portion 17 and the proximal end of the body, and passing the free end of said ancillary instrument 19 through one of the openings 6 so as to move the fractured bone fragments requiring repositioning. Such repositioning of the fractured bone fragments may optionally be monitored by inserting an arthrodesis camera inside the axial bore 4 of the pin 2.

It should be noted that the axis of the cylindrical portion 17 is substantially combined with the axis A of the pin in the immobilized position of the ancillary instrument 12 on said pin, and that the ancillary instrument 12 is designed and the various openings 15 are positioned such that, in the immobilized position of the ancillary instrument on the pin 2, the axis of each opening 15 formed on the guide portion 13 is combined with the axis of a through-hole 5 formed in the body of said pin.

The surgeon then produces bone bores across from the through-holes 5 of the pin 2 in which osteosynthesis screws are designed to be inserted to assemble fractured fragments to the main part of the calcaneum. These bores are made using a suitable ancillary instrument, such as a drill, whereof the drill member is designed to slide along the drill bushings 16.

Lastly, the surgeon inserts osteosynthesis screws 20 into the bone bores previously made and the corresponding through-holes 5 using a suitable ancillary instrument, such as a screwdriver 21.

It should be noted that the drilling of the bone bores and the screwing of the osteosynthesis pins may be guided using guide pins 22 previously implanted in the fractured bone fragments or in the main part of the calcaneum.

The invention is of course not limited solely to the embodiments of this osteosynthesis pin described above as examples, but on the contrary encompasses all alternative embodiments.

The invention claimed is:

1. A calcaneal osteosynthesis pin for the fracture of a calcaneum, made up of a cylindrical hollow body having an inner diameter constant over substantially the entire length of the body, the body comprising:
   an axial bore extending over the entire length of the body,
   a plurality of through-holes staggered longitudinally relative to one another and intended for attachment screws to pass therethrough,
   two diametrically opposite oblong openings suitable for an ancillary instrument to pass therethrough for repositioning fractured bone fragments, each oblong opening extending over a length corresponding to at least 40% of the length of the calcaneal osteosynthesis pin, and
   a distal tip, the distal tip of the body comprising a plurality of distal teeth configured to make a bone borehole in the calcaneum during the insertion of the calcaneal osteosynthesis pin in the calcaneum.

2. The calcaneal osteosynthesis pin according to claim 1, wherein each oblong opening extends substantially parallel to the axis of the calcaneal osteosynthesis pin.

3. The calcaneal osteosynthesis pin according to claim 1, wherein each through-hole has an axis extending substantially perpendicular to the axis of the calcaneal osteosynthesis pin, the axes of the through-holes being substantially parallel.

4. The calcaneal osteosynthesis pin according to claim 3, wherein each oblong opening is oriented at an angle comprised between 80 and 100° relative to the axes of the through-holes of the calcaneal osteosynthesis pin.

5. The calcaneal osteosynthesis pin according to claim 1, wherein the body includes angular indexing means for angularly indexing an ancillary instrument configured to implant said calcaneal osteosynthesis pin.

6. The calcaneal osteosynthesis pin according to claim 5, wherein the angular indexing means include an indexing slot emerging in a proximal end of the calcaneal osteosynthesis pin and with an axis substantially parallel to the axis of the through-holes.

7. The calcaneal osteosynthesis pin according to claim 1, wherein the body comprises fastening means configured to cooperate with complementary fastening means provided on an ancillary instrument configured to implant said calcaneal osteosynthesis pin.

8. The calcaneal osteosynthesis pin according to claim 7, wherein the axial bore comprises a threaded portion forming the fastening means, and the inner diameter of the body at the apices of the threads of the threaded portion substantially corresponds to the inner diameter of the body outside the threaded portion.

9. The calcaneal osteosynthesis pin according to claim 1, wherein each oblong opening includes a proximal opening end and a distal opening end, the proximal opening end of each oblong opening are located substantially equidistant from a calcaneal osteosynthesis proximal end and the distal opening end of each oblong opening are located substantially equidistant from a calcaneal osteosynthesis pin distal tip.

10. The calcaneal osteosynthesis pin according to claim 1, wherein the body has an inner diameter constant over the entire length of the body.

\* \* \* \* \*